United States Patent [19]

Bertin

[11] Patent Number: 5,320,625
[45] Date of Patent: Jun. 14, 1994

[54] APPARATUS AND METHOD FOR IMPLANTING A PROSTHETIC ACETABULAR CUP AND THEN TESTING THE STABILITY OF THE IMPLANT

[76] Inventor: Kim C. Bertin, 1879 Ridgehollow Dr., Bountiful, Utah 84010

[21] Appl. No.: 7,101

[22] Filed: Jan. 21, 1993

[51] Int. Cl.⁵ ............................................. A61F 5/04
[52] U.S. Cl. ...................................... 606/91; 606/99; 623/22
[58] Field of Search ................ 606/53, 86, 91, 99, 606/100; 128/898; 623/16, 22

[56] References Cited

U.S. PATENT DOCUMENTS

| | | | |
|---|---|---|---|
| 4,475,549 | 10/1984 | Oh . | |
| 4,716,894 | 1/1988 | Lazzeri et al. . | |
| 4,795,469 | 1/1989 | Oh | 623/22 |
| 4,922,898 | 5/1990 | Dunn | 606/85 |
| 4,955,325 | 9/1990 | Zarnowski et al. | 623/22 |
| 4,994,064 | 2/1991 | Aboczky | 606/91 |
| 5,030,221 | 7/1991 | Buechel et al. | 606/91 |
| 5,037,424 | 8/1991 | Aboczky | 606/91 |
| 5,049,158 | 9/1991 | Engelhardt et al. | 623/22 |
| 5,061,270 | 10/1991 | Aboczky | 606/91 |
| 5,064,427 | 11/1991 | Burkinshaw | 606/99 |
| 5,108,488 | 4/1992 | Gautier | 623/22 |
| 5,116,339 | 4/1992 | Glock | 606/91 |
| 5,127,920 | 7/1992 | MacArthur | 623/22 |
| 5,156,626 | 10/1992 | Broderick et al. | 623/22 |
| 5,171,324 | 12/1992 | Campana et al. | 623/23 |
| 5,211,665 | 5/1993 | Ku | 623/22 |

Primary Examiner—Stephen C. Pellegrino
Assistant Examiner—Jeffrey A. Schmidt
Attorney, Agent, or Firm—Workman Nydegger Jensen

[57] ABSTRACT

An implantation instrument and methods for reliably implanting a prosthetic acetabular cup in the acetabular area of the pelvic bone during a total prosthetic hip implant operation are disclosed. Such implantation device and methods also provide means for determining the adequacy or strength of the implant.

The implantation device includes means for receiving an implantation force from, for example a mallet, and imparting this force to press fit the prosthetic acetabular cup into a recess formed in the acetabular area of the pelvic bone. The apparatus also includes means for testing the strength or adequacy of the acetabular cup implant by receiving and imparting a torquing moment. Finally, the apparatus includes an alignment arm which is laterally displaced from the longitudinal axis of the apparatus, and selectively fixed or rotatably connected, in order to implant the prosthetic acetabular cup in the desired orientation.

The prosthetic acetabular cup contains a threaded recess therethrough, while the implantation instrument contains a threaded tip, for releasably connecting the acetabular cup and the implantation device. The cup is able to withstand forces associated with the steps of applying an implanting force and a torquing moment to test the stability of the implant.

58 Claims, 5 Drawing Sheets

APPARATUS AND METHOD FOR IMPLANTING A PROSTHETIC ACETABULAR CUP AND THEN TESTING THE STABILITY OF THE IMPLANT

BACKGROUND

1. Field of the Invention

This invention relates to apparatus and methods for the implantation and subsequent testing of the acetabular cup portion of an artificial hip joint. More particularly, the invention relates to improved apparatus and methods for reliably implanting and testing the strength of the implant of the acetabular cup component of a hip joint.

2. Relevant Technology

The hip is one of the most versatile joints of the human body and serves an essential function in allowing an individual to lead a normal life. The human hip joint performs its function much better than many devices heretofore designed by human engineers, and can withstand forces which are not readily apparent to those unfamiliar with orthopedics and kinesiology. For example, during ordinary walking, the hip joint is routinely subjected to dynamic forces nearly four times greater than a person's body weight. The dynamic forces on the hip joint may be as great as ten times the person's body weight during activities such as running or jumping.

When functioning properly, the bones of the hip joint move together with very little friction. To function properly, a healthy hip joint requires an intact layer of hyaline cartilage, the material which makes up the articular cartilage on the opposing surfaces of the joint. Also, the bones of the joint must be in proper alignment and the synovial membranes must produce suitable amounts of lubricating (synovial) fluid. Furthermore, the joint structures must prevent the bones from being placed in an abnormal position.

The human hip joint is shown in FIG. 1, which is an anterior (that is, taken from the front of the body) cross-sectional view of the human hip. The semi-circular shape of the acetabulum 10 can be seen. The upper leg bone, or femur 12, which can be seen just below the ilium 14, is the longest and strongest bone in the body. The upper end of the femur is provided with a spheroidally shaped head 16, a neck 18, a greater trochanter 20, and a lesser trochanter 22. The femoral head 16 is shown in FIG. 1 in a "normal" relationship with the acetabulum 10. It should be appreciated that FIG. 1 is not intended to show the exact structures of the hip joint, since the structure varies somewhat from individual to individual, but to show the relationship of the major components which make up the hip.

FIG. 1 also illustrates the acetabulum articular cartilage 24 and femoral head articular cartilage 26. A space 28 is shown extending between the entirety of the two articular cartilage surfaces. This "joint space" 28 may or may not be present in a particular hip, depending upon the condition of the hip. Normally, the articular cartilage 24 is smooth and intact. When the articular cartilage 24 is damaged, however, pain and an accompanying restriction of motion can often result.

The femur 12 is provided with a femoral neck 18 which may be up to 5 cm long. The femoral neck 18 separates the shaft of the femur 12 from the femoral head 16. This arrangement allows the femur a substantial degree of movement without interference from the bones making up the pelvis.

The greater trochanter 20 serves as an attachment point for various muscles and ligaments. The lesser trochanter 20 serves a similar purpose. Round ligament 30 is thought to provide a passage for the blood vessels to the femoral head 16 and also to assist with spreading of synovial fluid over the articular cartilage surfaces 24, 26 to lubricate and nourish the cartilage.

The versatility of the hip joint can be appreciated by realizing that the normal range of motion includes flexion and extension (rotation in forward and rearward directions, respectively) and adduction and abduction (motion towards the center line of the body and away from the center line of the body, respectively).

While the hip joint generally serves its purpose very well, various disorders of the hip can cause a great deal of pain and loss of mobility and function. Some hip disorders are congenital, that is, they are present at birth. Other disorders of the hip are brought on by bacterial infection, which can occur at any age. Perhaps the most widespread disorder of the hip is arthritis. The term "arthritis" is generally used as a common name for the effects of several degenerative hip disorders.

Of the various types of arthritis, osteoarthritis is perhaps the most common. Osteoarthritis is a degenerative "wear and tear" process that affects substantial numbers of people. The final result of unchecked osteoarthritis is damaged articular cartilage which, in many cases, causes extreme pain as the damaged surfaces are rubbed together during joint movement. It has been estimated that between 8% and 15% of the population of developed countries, with higher percentages prevalent in older populations, suffer some degree of osteoarthritis.

One disorder of the hip which appears to lead to osteoarthritis is known as "congruence." Congruence occurs when the shape of the femoral head and the shape of the acetabular socket become matched so that the dome area of the acetabulum 10 and the femoral head 16 are nearly always in contact. Congruence of the hip can cause increased wear on the joint surfaces. Several of these disorders and other conditions are explained in more detail hereinbelow. Osteoarthritis may also involve the development of abnormal bony outgrowths on the joint surfaces known as osteophytes. An osteophyte consists of a lump of "cancellous" tissue (tissue having a lattice structure similar to the spongy tissue of the bone) which is capped by a sheet of soft tissue. Commonly, cysts also form on the femoral head and in the acetabulum with the hip joint. These cysts are often formed just under the articular cartilage and result in a great deal of pain.

Generally, osteoarthritis affects people past the age of 60 years without providing an easily recognizable, single cause. However, it may also develop in younger people, usually due to a congenital condition or disease. Furthermore, traumatic injury may cause the development of an osteoarthritic condition.

Another hip disorder is osteonecrosis, or death of a portion of a bone, which is due to an insufficient blood supply to part of, or the whole of, a bone. Osteonecrosis may be brought on by excessive alcohol consumption, administration of particular drugs, old age, or as a result of osteoarthritis.

In the prior art, several methods have been used for alleviating the pain and improving the function of a hip joint afflicted with a degenerative disorder such as osteoarthritis. Perhaps the earliest surgical procedure used to reduce pain due to a disorder of a hip joint was "ankylosing," or fusing the joint. This alternative, generally called "arthrodesis," alleviates pain in a diseased hip joint but also prohibits proper function of the joint. Thus, arthrodesis is generally not an acceptable procedure of relieving hip pain for most patients. In fact, hip surgery is quite often carried out in order to remedy a hip which has become ankylosed, stiff, or immovable.

In some other cases, "debridement" of a hip joint may be helpful. Debridement of the joint usually consists of removing unwanted bony spurs and loose pieces of bone and cartilage within the joint cavity. While this procedure is helpful in some cases, the most common cause of pain and loss of function is due to degeneration of the hip joint rather than abnormal growths or debris in the joint.

Osteotomy, which generally refers to the cutting and resetting of a bone, has also been used in an attempt to alleviate pain and restore function of the hip joint. By cutting and resetting the femur, for example, it may be possible to reorient the femur head 16 within the acetabulum 10 such that portions of the femur head 16 not affected by the degenerative disorder are used as weight-bearing surfaces. However, in the case of osteoarthritis, the surfaces of both the acetabulum 10 and the femur head 16 are generally involved in the degenerative condition. If the surface of the acetabulum 10 has been damaged, repositioning of the femoral head 16 will probably not provide relief.

Because of limitations of the foregoing procedures, one of the most common procedures used in treatment of hip disorders is the implantation of artificial joint components. This procedure is known as "arthroplasty," and has been one of the major areas of advancement in hip surgery during the past quarter century. Hip arthroplasty has included techniques known as interpositional arthroplasty, partial arthroplasty, and total arthroplasty.

Interpositional arthroplasty of the hip joint generally involves interposing a layer of material between the two opposing articular surfaces of the joint. For example, materials such as muscle, fibrous tissue, celluloid, silver plates, rubber sheets, magnesium, zinc, decalcified bones, and pig's bladder have all been used in interpositional arthroplasty of various joints. Cup-shaped structures made from gold foil, glass, or VITALLIUM ® (a cobalt-chromium alloy) have also been interposed between the femoral head 16 and the acetabulum 10. Even further attempts have been made to encase the femoral head 16 within a metallic shell and also line the acetabulum 10 with a cup comprised of a plastic-like material.

Partial arthroplasty involves the replacement of one of the two opposing articular joint surfaces 24, 26. For example, this procedure is used where the femoral head 16 has been damaged but the acetabulum 10 is otherwise normal. In such a case, it may be beneficial to replace the femoral head 16 with an artificial prosthesis which will work in conjunction with the natural acetabulum 10. Partial arthro-plasty procedures have met with only limited success.

The most common arthroplasty procedure used to alleviate pain and restore hip function is total hip arthroplasty, also called a total hip replacement. While many different styles of hip replacement prosthesis have been implanted in patients, they generally resemble the prosthesis illustrated in FIG. 2. FIG. 2 also illustrates the femur 12 and a portion of the pelvis in cross-section in order to best show how the components of a total hip replacement are implanted in the body.

FIG. 3 is an exploded view of the main components of a prosthetic hip implant. These include an acetabular structure 50, including an outer acetabular cup 52, which often has a plurality of holes 54. The outer acetabular cup fits into an acetabular recess 51 within the pelvic bone 53, which is formed by removing enough of the surrounding bone and other tissue in the acetabular region of the pelvic bone 53 to create a conforming fit. An inner acetabular cup 56 fits inside the outer acetabular cup 52 and is held in place by means known in the art. The inner acetabular cup 56 also includes a generally hemispherical space 58 into which an artificial femoral head is placed.

FIG. 3 also shows a femoral structure 60, including a femoral head 62 connected to a femoral neck 64 and a stem 66, which is inserted into a hollowed recess of the femur 12.

The outer acetabular cup is generally made of a durable metal, while the inner acetabular cup is made of a smooth yet durable plastic, such as polyethylene. The femoral head 62 is generally made of a hard, durable metal with a smooth surface to interface with the polyethylene surface of the inner acetabular cup 56.

Conventional total hip replacement involves a complete internal amputation of the hip joint as suggested in FIG. 2. The conventional surgical procedure used during total hip replacement involves making a surgical incision to provide an approach to the hip. Once the hip is exposed, the joint is dislocated so that the femoral head 16 and acetabular socket 10 can be accessed. The femoral head 16 and neck 18 are then amputated. Often, the greater trochanter 20 is removed and reattached at a lower point by the use of wires 32. Once the femoral head 16 and neck 18 have been removed, the femoral canal (the central core of the bone, generally indicated as 34) is reamed so as to provide a cavity into which a stem 36 of a femoral component 38 may be inserted. The femoral canal 34 is reamed so that its diameter is significantly larger than the diameter of the femoral component stem 36.

One commonly accepted method of fixing the femoral component 38 to the femur 12 is by polymethylmethacrylate (PMMA), which is a two-component acrylic cement that has the advantage of exhibiting a rapid setting time. After mixing the two components, the femoral canal 34 is "packed" with unset PMMA. The stem 36 of the femoral component 38 is then inserted into the femoral canal 34 and the femoral component 38 is held in the proper position until the PMMA has set. Since the femoral canal 34 has been reamed out to a larger diameter than the stem 36 of the femoral component 38, the PMMA cement serves as a "grout" 37 which interfaces between the stem 36 and the remaining bone.

The femoral component 38 is available in varying sizes and styles, but nearly all of those presently used include a stem 36, a neck 40, and a ball-shaped head 42 similar to the analogous components of an actual femur 12 pictured in FIG. 1. Most of the prosthetic femoral components which are presently used are fabricated from a cobalt-chromium steel alloy or a titanium alloy.

Implantation of the acetabular components 44 also requires significant alteration of the bone structure. The acetabulum 10 is first reamed out to provide a cup-shaped cavity into which an outer acetabular cup 46 will be fixed. An inner acetabular cup 48 fits within the outer acetabular cup 46. Conventional acetabular components 44 used in total hip replacements are relatively large. Presently, most inner acetabular cups 48 are fabricated from ultra-high molecular weight polyethylene (UHMWP). The outer acetabular cup 46 is fixed within the reamed out cavity by PMMA adhesive, which once again serves as a grouting cement. The inner acetabular cup 48 is press-fitted within the outer acetabular cup 46.

After the femoral component 38 and the acetabular components 44 have been implanted, the greater trochanter 20, if previously removed, is reattached using the wires 32 at a point lower on the femur 12 so as to provide a mechanical advantage more favorable to the total hip prosthesis. The joint is then reduced and the surgical incision closed.

As mentioned previously, the stresses on the hip joint during ordinary activities are very high. During strenuous activities those stresses are increased several fold. These high stresses result in several mechanical difficulties in a patient fitted with a conventional total hip prosthesis. For example, it is not uncommon for the femoral component 38 to become dislocated from the acetabular components 44. Alternatively, the components may fail (i.e., fracture or break) due to the stresses placed upon them. A common difficulty is loosening of the components from the surrounding bone. Generally, problems such as loosening or failure are particularly acute with the femoral component. Nevertheless, problems with implanted prosthetic acetabular cups have developed over time which were not apparent at first.

For example, where bone cement has been used, there have been problems with the resorption of the surrounding bone next to the bone cement. This is because the body recognizes the bone cement as a foreign body, causing the body's immune system to attack the surrounding area, including the bone. When this occurs, the prosthetic acetabular cup connection becomes very weak and can fall out.

Another method of stabilizing acetabular cup implants involves the use of surgical screws, which are screwed into underlying bone through holes in the prosthetic acetabular cup. While a generally secure way of fastening the prosthetic acetabular cup, surgical screws can introduce infection into the patient's tissue, irritate and damage nerves, and rupture blood vessels, causing pain and other damage to the surrounding tissue. Similar problems occur with the use of surgical pegs, which generally require the drilling of holes into the surrounding bone area.

An example of an acetabular cup using pegs to stabilize an acetabular cup implant is found in U.S. Pat. No. 5,127,920 to MacArthur. A similar configuration can be found in U.S. Pat. No. 5,108,448 to Gautier, wherein a cup with numerous spike-like protrusions is inserted into the acetabular area. While these cups undoubtedly result in a fairly reliable fit, at least in a rotational sense, they possess the various problems associated with using spikes or pegs.

More recently, surgeons have begun to perform less complicated prosthetic acetabular cup implants by press-fitting the prosthetic acetabular cup into a slightly smaller recess within the acetabular area of the pelvic bone. The results have been mixed. If a cup implant is not sufficiently tightly fit, it is less likely to stay in place. Moreover, simply and blindly making a tighter fit has many risks, including the possibility of fracturing the pelvis bone, or the problem of "rim fitting."

In the case of rim fitting, the implanted cup makes tight contact with the outer rim of the recess but fails to make abutting contact with the lower portion of the recess. Thus, a rim fit may appear adequate although difficulties may appear due to the inability of bone to grow across the gap where an implanted acetabular cup has failed to "bottom out" against the surface of the lower portion of the recess.

The safest and least complicated prosthetic acetabular cup implant is one which is relatively round but which has a roughened or irregular surface. If the cup is adequately press fitted, surrounding bone will grow into the irregularities in the surface of the cup, resulting in a very strong and secure acetabular cup implant.

Examples of devices which are used to implant prosthetic acetabular cup implants are disclosed in U.S. Pat. No. 5,061,270 to Aboczki, U.S. Pat. No. 5,037,424 to Aboczki, U.S. Pat. No. 5,030,221 to Buechel et al., and U.S. Pat. No. 4,994,064 to Aboczki. Each of these implantation devices is made of rigid materials, are capable of imparting a strong implantation force to drive the cup implant into a recess in the acetabular area, and are able to position the cup so that the implanted cup is in the proper orientation. Nevertheless, none of these devices gives the doctor any indication as to the sufficiency or tightness of the acetabular cup implant. Thus, although each of these devices can often result in successful cup implants, there remains a certain level of uncertainty regarding the reliability of the implant.

Once total hip replacement has occurred, revision of the procedure (revision being the term used to describe when the prosthesis is replaced) can be extremely due to the amount of bone mass which was removed during the original procedure, as well as the extreme invasiveness of the procedure. If there were a reliable way to test the stability of the implant, the surgeon would then be able to take remedial measures such as using secondary methods of securing the implanted cup before sewing the patient up.

From the foregoing, it will be appreciated that what are needed are apparatus and methods for reliably implanting an acetabular cup that will result in a reliable implant, but which avoids the complications associated with using bone cement.

It will also be appreciated that it would be an improvement over the prior art to provide apparatus and methods for reliably implanting an acetabular cup that will result in a reliable implant, but which avoids the complications associated with using surgical screws.

Further, it would similarly be an improvement over the prior art to provide apparatus and methods for reliably implanting an acetabular cup that will result in a reliable implant, but which avoids the complications associated with using surgical pegs.

It would yet be a further advancement in the art if such apparatus and methods for implanting a prosthetic acetabular cup resulted in a reliable implant but which also included a way to test the stability of the implant to allow the surgeon the option of using secondary securement means known in the art if necessary.

Finally, it would yet be an even greater improvement over the prior art if such implantation and testing methods could be carried out with a minimal amount of equipment and in a minimum amount of time.

Such apparatus and methods are disclosed herein.

BRIEF SUMMARY AND OBJECTS OF THE INVENTION

The present invention relates to improved apparatus and methods for implanting a prosthetic acetabular cup implant and then testing the stability or adequacy of that implant. The apparatus includes an implantation instrument made of a rigid material which can be releasably connected to a prosthetic acetabular cup at one end, and which is designed to receive an implantation force at a distal end, preferably by means of a mallet or hammer. The implantation instrument is generally a thin, cylindrically shaped tool made of hard, impact-resistant metal. The generally cylindrical shaft of the instrument has a central longitudinal axis.

In addition, the prosthetic acetabular must be particularly adapted so that it may be releasably connected to the implantation device. In addition, the cup and the connection means within the cup must be able to withstand both an implantation force imparted by the implantation instrument and a subsequently applied torquing moment used to test the stability of the cup implant.

The implantation instrument also includes a prosthesis orientation bar laterally displaced from the central shaft of the implantation instrument. The prosthesis orientation bar is displaced from the central shaft of the implantation device at an appropriate angle so that the acetabular cup can be implanted into the proper orientation. The prosthesis orientation bar is used to ensure that the angle of abduction of the implanted acetabular cup ranges from between about 30° to about 45° depending on the patient.

In addition, the prosthesis orientation bar further includes a pair of prosthesis orientation legs generally disposed in a V-shaped orientation nearer a distal end of the orientation bar. The pair of prosthesis orientation legs are used to ensure that the angle of anteversion of the implanted acetabular cup ranges from between about 10° to about 20°. (One of the legs is used when the right hip is being treated, while the other is used when the left hip is being treated).

The implantation instrument includes locking means for selectively locking or unlocking the prosthesis orientation arm so that the implantation instrument can be rotated while keeping the prosthesis orientation arm relatively immobile relative to the patient. This allows for easier removal of the implantation device when unscrewing it from the acetabular cup after a successful implantation without the prosthesis orientation bar getting in the way.

The implantation instrument includes means for interfacing the instrument with a torquing device, preferably a torque wrench, which can measure the amount of torque being applied. Once a prosthetic acetabular cup has been implanted into a prepared recess in the acetabular area of the pelvic bone by impacting the implantation device with a hammer or mallet, a torquing moment is applied to the implantation device to test the adequacy or firmness of the implant.

If the implant can resist rotation when subjected to a predetermined torquing moment, the implant is generally considered to be adequately strong. However, if the acetabular cup rotates when subjected to less than the predetermined amount of applied torque, the implant is generally considered to be inadequate. The amount of torque which the implanted acetabular cup must resist is dependent upon a number of factors, including but not limited to the patient's weight, bone structure, or activity level.

If the implant is determined to be inadequately secure, the surgeon can take remedial measures, such as repreparing the acetabular recess and/or inserting a slightly larger acetabular cup which will result in a tighter press fit. Often, the same acetabular cup can be reimplanted with satisfactory results just by making a slightly deeper bore within the acetabular recess, which usually exposes softer, more adhesive bone. In other cases it may be necessary to insert a slightly larger cup which will fit more tightly within the acetabular recess. Finally, some cases may require the repreparation of the recess and a larger cup.

Alternatively, the surgeon can use secondary securing means, such as employing a small amount of bone cement, or by using surgical screws or surgical pegs. Nevertheless, it should be understood that the preferable securing means will be the press fit of the implanted cup, and that the secondary securing means are merely added to assist, not take the place of, the press fit.

If an acetabular cup has been successfully press fit, and has generally "bottomed out" within the recess, the chances are very good that the surrounding bone will quickly grow into and intertwine with the surface of the prosthetic acetabular cup, thus locking it in place. This results in a much more reliable and durable prosthetic cup implant.

During the step of applying torque to the implantation instrument to determine the strength of the acetabular cup implant, it is often preferable to also apply a downward stabilization force in the same general direction as the implantation force. This prevents the torquing force from rotating the acetabular cup into a non-aligned position. However, this stabilization force may tend to oppose the torquing moment being applied, which can falsely increase the observed force being applied to the implanted acetabular cup.

Thus, it is often preferable to use a knob which is rotatably connected to the impact head during the torquing step so that the downward force exerted by a doctor during a torquing step will not translate into a force opposing the applied torquing moment. This prevents obtaining a false positive reading. For example, a downward stabilizing force by the doctor which increases the apparent torque which the acetabular cup is presumed to resist may lead a surgeon to conclude that a poor implant is actually adequate. In reality, the implant may not be able to resist the same level of torque once the added resistance from the downward stabilizing force is removed or factored out. The rotatably connected knob allows the surgeon to apply a downward stabilizing force while allowing free rotation of the implantation device beneath the knob.

From the foregoing, it should be appreciated that an object of a present invention is providing an apparatus and methods which can be used to implant an acetabular cup and then test the stability or strength of the implant.

Another object of the present invention is to provide apparatus and methods which can be used to reliably implant an acetabular cup with a generally rounded surface without having to use bone cement.

Yet another object of the present invention is providing apparatus and methods which do not generally require the use of surgical screws, which avoids the problems associated with such surgical screws. Still another object of the present invention is the ability to obtain reliable acetabular cup implants without the general use of surgical pegs, and the problems associated with surgical pegs.

Finally, an object of the present invention is providing apparatus methods for both reliably inserting an acetabular cup and testing the strength of the implant using a minimum of equipment and in a relatively short period of time.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above-recited and other advantages and objects of the invention are obtained can be better understood, a more particular description of the invention briefly described above will be rendered by reference to specific embodiments thereof which are illustrated in the appended drawings and which represent the best mode presently contemplated for carrying out the present invention. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

The present invention relates to apparatus and methods used in a prosthetic hip implant operation. More specifically, the present invention relates to apparatus and methods which can be used to reliably implant a prosthetic acetabular cup into the acetabular area of the pelvic bone generally without the use of secondary securing means, such as bone cement, surgical screws, or surgical pegs. In the event that such secondary securement means are necessary to secure an implanted acetabular cup, the apparatus and methods of the present invention would also work to test the stability of the secondarily secured implant.

In addition, the apparatus and methods of the present invention allow the surgeon to also test the adequacy and strength of the acetabular cup implant. This testing is generally carried out by applying a torquing moment to the implantation device by means of a torque wrench. A successful acetabular cup implant is determined if the cup can resist rotation when subjected to a predetermined torquing moment. If the acetabular cup implant can resist the torquing moment and remain immobile, the operation is considered successful, the implantation device is removed, and the operation then proceeds as normal.

However, in the event that the implant is insufficiently tight and cannot resist a predetermined torquing moment, the surgeon may exercise one of the many methods known in the art to help secure the acetabular cup implant within a recess formed within the acetabular area. Prior means for determining the strength of the femoral portion of a prosthetic hip implant are disclosed in U.S. Pat. No. 4,922,818 to Dunn. However, the device in Dunn does not test the resistance to torque of the actual femoral implant; instead, it tests the resistance to torque of a preimplant rod inserted into a recess or bore in the center of the femur, thus determining the adequacy of the bore. Thus, the device in Dunn merely tests the propensity of the bore to resist rotation of an implanted femur, but not the actual implant itself.

Figure 1:
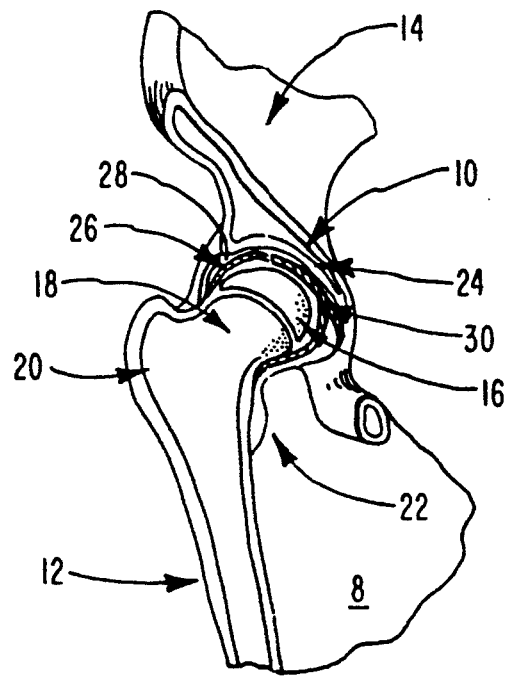
FIG. 1 is a cross-sectional view showing the major structures of the human hip joint.
Figure 2:
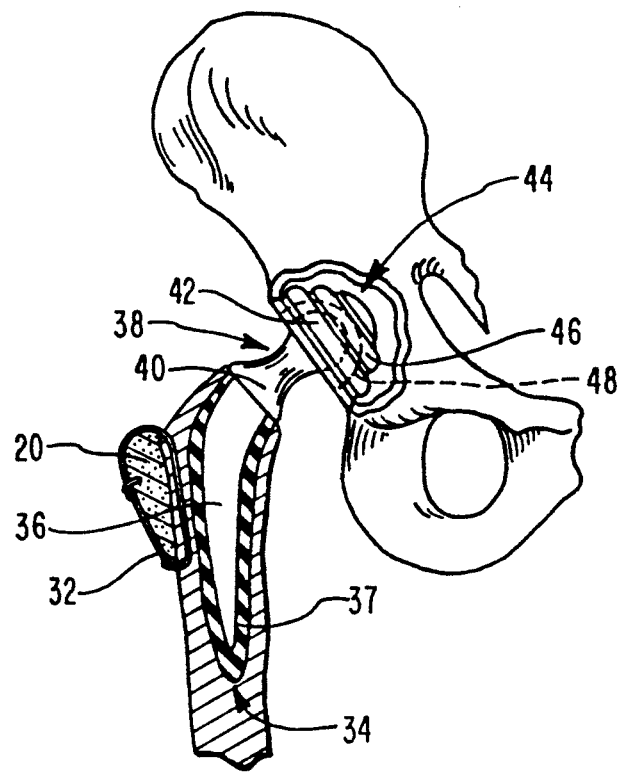
FIG. 2 is a partial cross-sectional view of the human hip in which a total hip replacement common in the prior art has been implanted to replace the natural hip joint.
Figure 3:
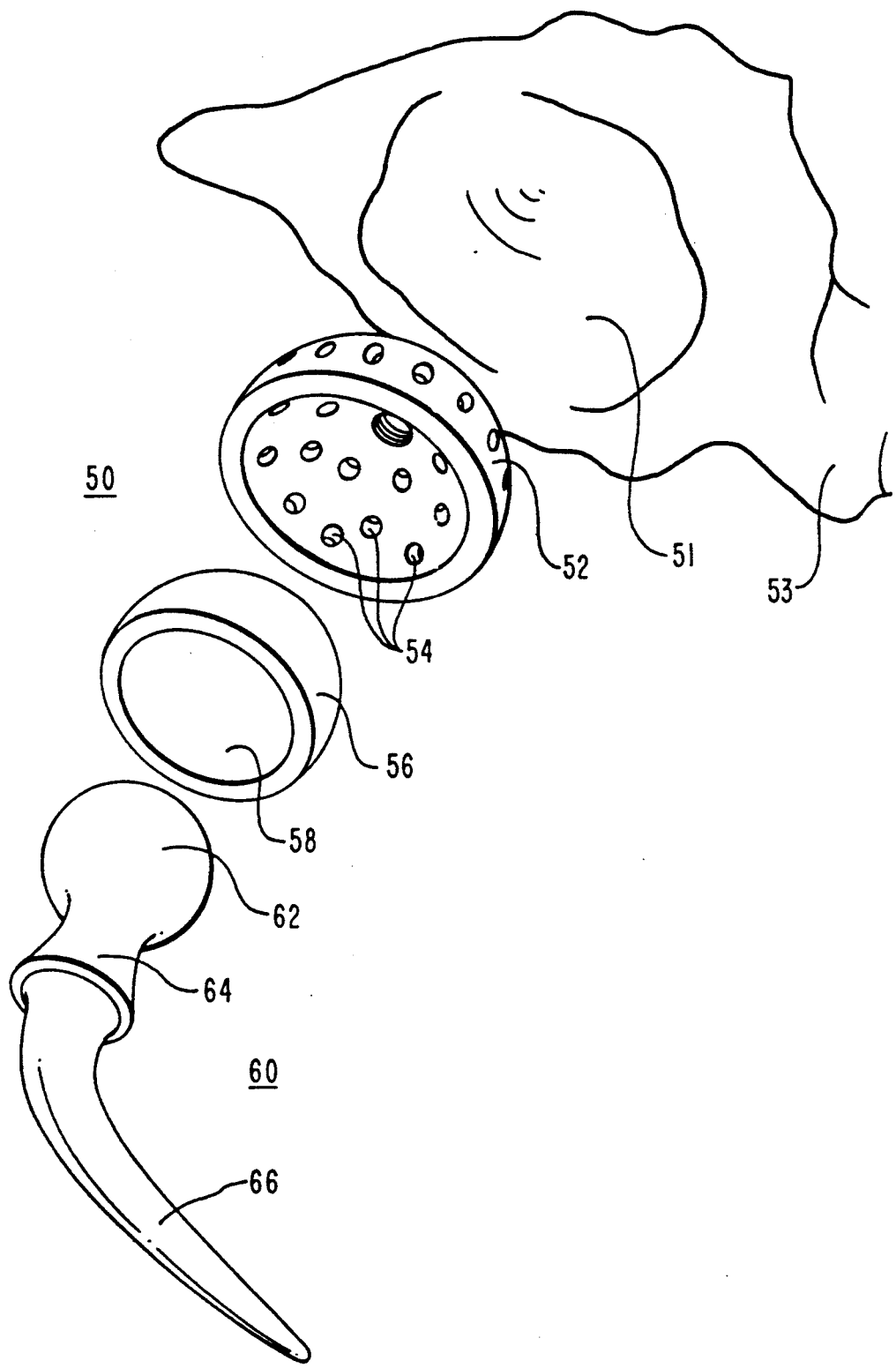
FIG. 3 is an exploded perspective representation showing the various elements of a total prosthetic hip joint replacement set as they would fit within a recess in the acetabular area of the pelvis bone.
Figure 4:
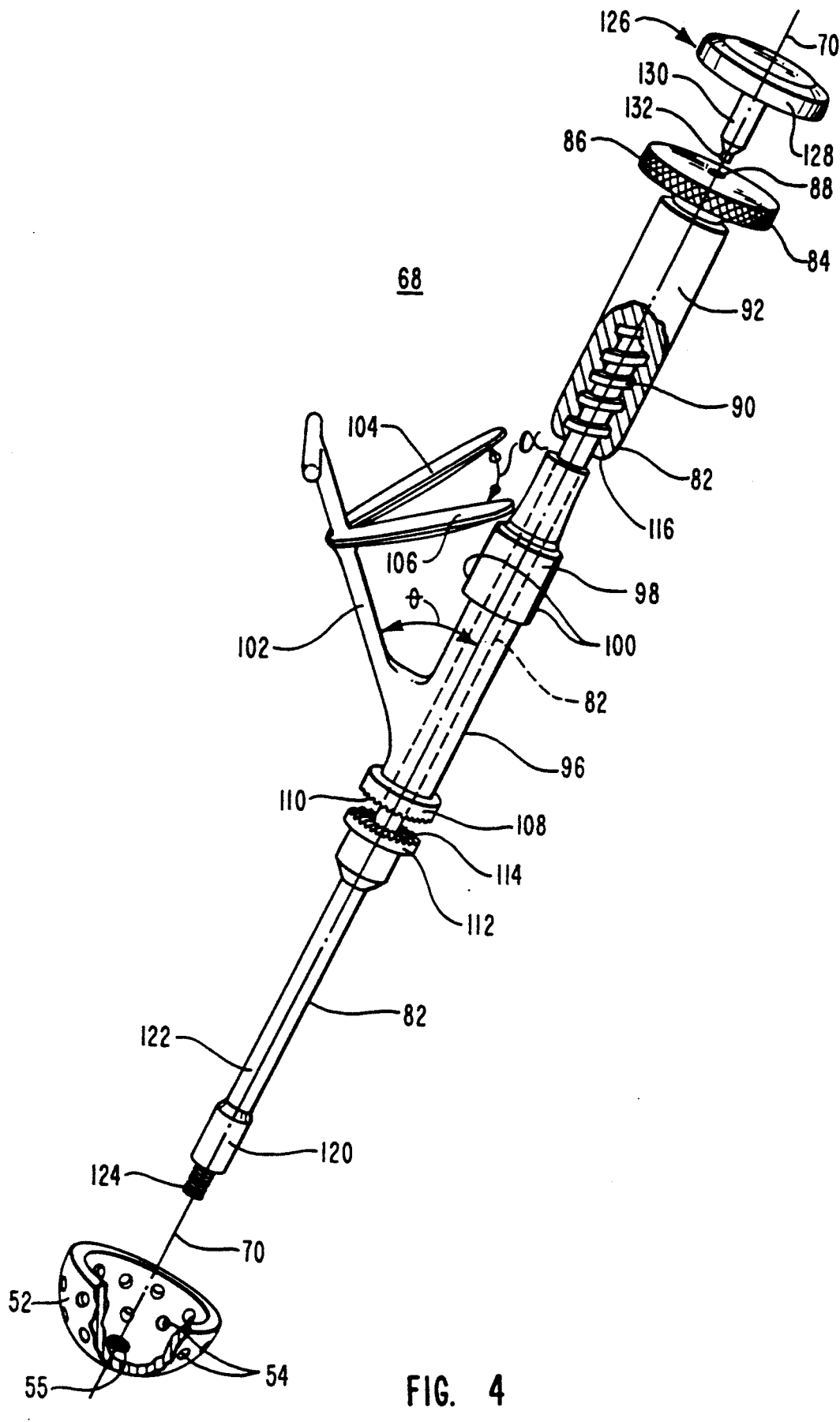
FIG. 4 is an exploded view of an implantation device of the present invention and an acetabular cup.

FIG. 4 shows an exploded view of a presently preferred embodiment of the apparatus of the invention suitable for use in the implantation of a prosthetic acetabular cup according to the present invention. As in the prior art, the preferable acetabular cup 52 is generally round, having a hemispherical shape and a hollow interior. The acetabular cup 52 can optionally have one or more holes 54 for the insertion of surgical screws, pegs, etc. to help secure an implanted acetabular cup 52. The acetabular cup 52 includes a recess 55 which corresponds to a tip of an implantation instrument for releasably connecting the cup to the implantation instrument 68, as discussed below.

In a preferred embodiment, the recess 55 is threaded to receive a threaded tip of an implantation instrument, as more fully discussed below. Alternatively, the recess 55 can have a shape which corresponds to the shape of a tip of an implantation instrument used to implant the particular acetabular cup 52. For example, the recess 55 can be hexagonal or star-shaped, or have a Phillips-type shape. The only limitation is that the recess 55 be capable of receiving a torquing force sufficiently strong to adequately test the stability of the implanted cup 52.

The acetabular cup 52 must be designed so that it will be able to withstand the forces associated with both the implantation step, as well as the step of applying a torquing moment to test the stability of the cup implant. Thus, the thickness of the cup in the immediate area around the recess 55 must be sufficient to give the acetabular cup 52 sufficient strength so that it will not break or bend during the step of implanting the cup when strong downward forces are applied to the cup. In addition, the cup must be made of a sufficiently hard and durable metal so that the walls of the recess 55 will not be stripped or sheared when subjected to the strong torquing forces during the step of determining the stability of the implanted cup 52.

It should be noted that each of the prior art references regarding implantation devices taught the use of a connecting adaptor that is interposed between the acetabular cups and the implantation devices disclosed therein. In the present invention, the designs of both the acetabular cup 52 and the implantation instrument set forth more fully below obviate the need for a connecting adaptor.

The implantation instrument 68 according to the present invention includes a central axis 70 and central shaft 82 disposed along the central axis 70. The central shaft 82 has two ends, one which is proximal to the acetabular cup 52 and one that is distal thereto. Fixedly attached at a distal end of the central shaft 82 is an impact head 84. The impact head 84 is generally large enough to receive the impact of a hammer or mallet used to impart an implantation force to the implantation device 68. The impact head 84 includes a circumferential surface 86 which is generally cross-hatched to create a surface which can be reliably gripped by a doctor during the procedure. On the top distal surface of the impact head is a shallow recess 88, the purpose of which will be discussed below.

Below the impact head, but also nearer the distal end of the central shaft 82, are widely spaced threads 90. In the general area of the threads is disposed a hollow actuating cuff 92 which is concentric to, and coaxial with, the central shaft 82 along the central axis 70. The actuating cuff 92 includes threaded recesses 94 which correspond to the threads 90 on the surface of the central shaft 82.

In the center region of the central shaft 82 is disposed a hollow intermediate sleeve 96 which is generally concentric to, and coaxial with, the central shaft 82 along the central axis 70. Disposed on the surface of the hollow intermediate sleeve 96 is a torquing flange 98, the purpose of which will be discussed below. The torquing flange 98 includes a pair of flat parallel sides 100.

A prosthesis orientation bar 102 is rigidly connected to the more proximal end of the hollow intermediate sleeve 96 and is laterally displaced with an angle $\theta$, which in a preferred embodiment is 45°. This angle is chosen based on the desired angle of abduction known in the art with respect to acetabular cup implants. Knowing the angle of displacement of the prosthesis orientation bar 102, the implantation device 68 can be positioned so that the prosthesis orientation bar extends into space at a predetermined angle relative to the surface of the operating bed, this second angle being calculated for each individual patient and dependent upon factors unique to each patient. The angle of the prosthesis orientation bar 102 relative to the surface of the operating table measures the angle of abduction of the implanted acetabular cup 52. In this manner, the surgeon can implant the acetabular cup 52 in the proper angle of abduction, which generally ranges between about 30°–45° depending on the patient. The desired angle of abduction is chosen based on a number of factors, such as hip stability and unique, complex changes in the anatomy of the individual patient being treated, all of which are well-known to those skilled in the art of prosthetic hip surgery.

Nearer the distal end of the prosthesis orientation bar 102 are disposed a pair of prosthesis orientation legs 104, 106 in a V-shaped configuration having an angle $\alpha$ therebetween, which are used by the surgeon to implant the acetabular cup 52 in the proper angle of anteversion. This angle is determined is chosen to correspond to the desired angle of anteversion of the implanted acetabular cup 52, which usually ranges between 15°–20°, but which can range from 10°–20°.

When an acetabular cup 52 is being implanted into the left hip, the implantation device is oriented so that the left prosthesis orientation leg is parallel to the torso of the patient. Similarly, when an acetabular cup is implanted into the right hip, the implantation device is oriented so that the right prosthesis orientation leg is parallel to the torso of the patient. In this manner, the surgeon can implant the acetabular cup in the proper angle of anteversion, which will correspond to the angle $\alpha$ between the V-shaped prosthesis orientation legs 104. The desired angle of anteversion is chosen based on a number of factors, such as hip stability and unique, complex changes in the anatomy of the individual patient being treated, all of which are well-known to those skilled in the art of prosthetic hip surgery.

At the extreme proximal end of the hollow intermediate sleeve 96 is a coupling clutch 108 having a plurality of locking teeth 110 disposed around the proximal side of the hollow intermediate sleeve 96. Corresponding to the sleeve coupling clutch 108 is a shaft coupling clutch 112 fixedly attached to the outer surface of the central shaft 82, which also includes a plurality of locking teeth 114 on the surface of the shaft coupling clutch 112.

When the sleeve coupling clutch 108 is in engaging contact with the shaft coupling clutch 112, the hollow intermediate sleeve 96 is rigidly affixed relative to the central shaft 82. Conversely, when the sleeve coupling clutch 108 and the shaft coupling clutch 112 are separated such that the sets of locking teeth 110, 114 are disengaged, the hollow intermediate sleeve 96 and the central shaft 82 enjoy free rotation relative to each other.

The locking or unlocking of the coupling clutches is controlled by the actuating cuff 92. More specifically, the hollow actuating cuff 92 has a lower cuff surface 116 at the proximal end, which engages and corresponds to the upper sleeve surface 118 of the hollow intermediate sleeve 96. As the actuating cuff 92 is rotated, it moves up or down the central shaft 82 depending upon the angle of the threads 90. As the hollow actuating cuff is moved toward the hollow intermediate sleeve 96, the lower cuff surface 116 engages the upper sleeve surface 118 and forces the hollow intermediate sleeve 96 downward until the sleeve coupling clutch 108 engages the sleeve coupling clutch 112, causing the locking teeth 110, 114 of each to become rotationally interlocked together. In this orientation, the hollow intermediate sleeve 96 is rigidly affixed to the central shaft 82.

As the hollow actuating cuff 92 is rotated such that it is moved away from the hollow intermediate sleeve 96, the hollow intermediate sleeve 96 can be moved such that the sleeve coupling clutch 108 is disengaged from the shaft coupling clutch 112. In this orientation, the hollow intermediate sleeve 96, which includes the alignment bar 102, is free to rotate relative to the central shaft 82. This allows the operating surgeon to orient the alignment bar 102 in the proper configuration just prior to applying the implantation force and the torquing moment, as more fully discussed below.

At the proximal end of the central shaft 82 is a connector tip 120 connected to the lower neck 122 of the central shaft 82. The connector tip 120 includes a shaft finger 124 which corresponds to the shape of the recess 55 of the acetabular cup 52. The shaft finger 124 is threaded in a preferred embodiment, but can also be hexagonal or star-shaped, or have a Phillips-type configuration. The only limitations being that the shaft finger 124 have a shape which corresponds to the shape of the recess 55 of the acetabular cup 52, and that the shaft finger be sufficiently durable to avoid being stripped or sheared when subjected to the strong torquing forces during the step of determining the stability of the implanted cup 52.

A stabilizing force adapter 126 is provided which is preferably about the same size and shape of the impact head 84 and includes a gripping disk 128, an axial rod 130, and an engagement tip 132 disposed at a proximal end of the axial rod 130. During use, the engagement tip 132 is inserted into the shallow recess 88 on the distal surface of the impact head 84, loosely connecting the impact head 84 and the stabilizing force adapter 126 in a rotatable configuration along the central axis 70.

Figure 5:
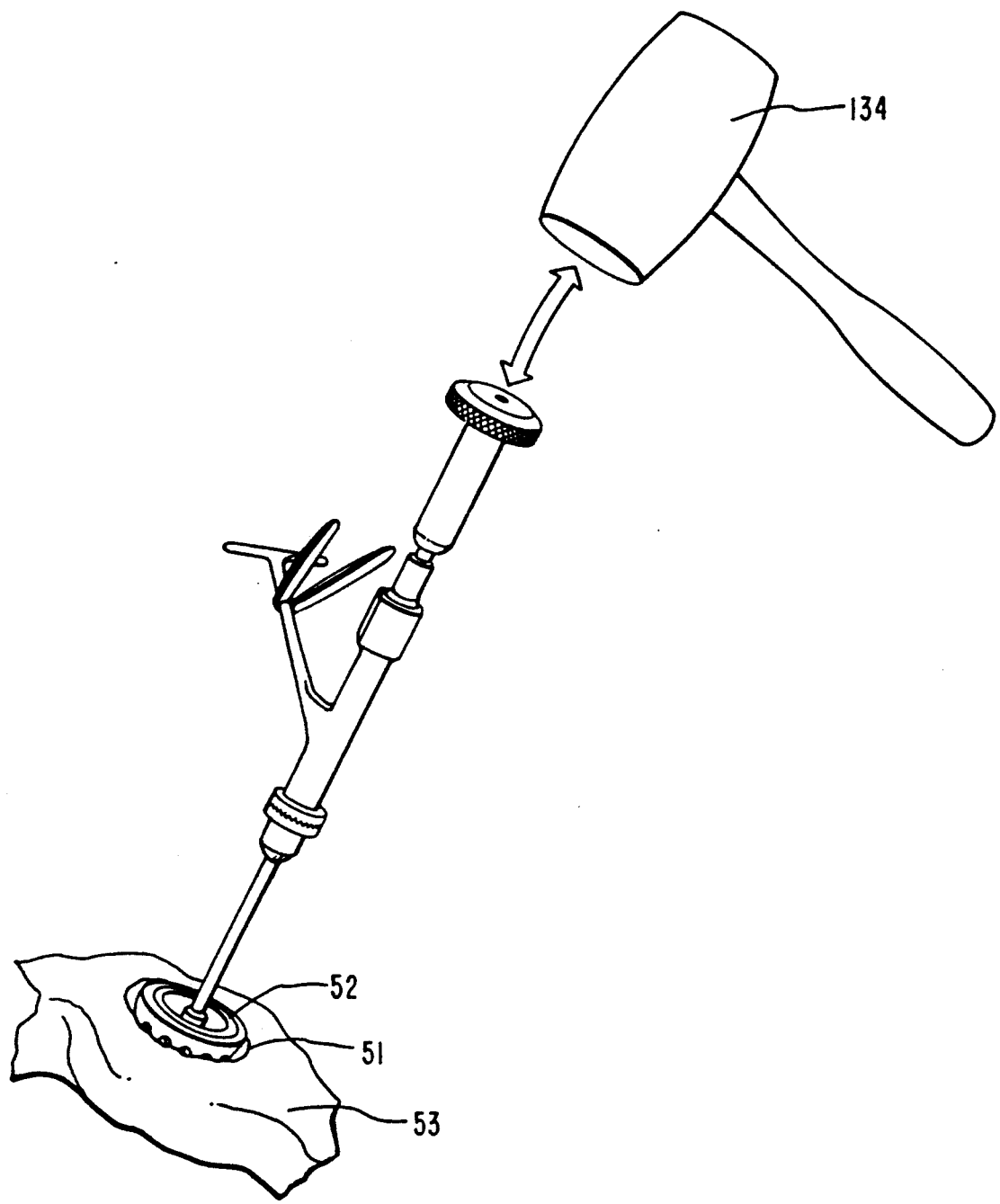
FIG. 5 is a view of an acetabular cup being implanted into the acetabular area of the pelvic bone using a mallet.

FIG. 5 shows the implantation instrument 68 in use to implant the acetabular cup 52. First, the implantation instrument 68 and acetabular cup 52 are engaged so that the shaft finger 124 of the connector tip 120 reliably engages the corresponding recess 55 of the acetabular cup 52. The hollow actuating cuff can be released, allowing the operating surgeon to rotate the orientation bar 102 into the desired configurating relative to the patient's hip.

Subsequently, an implantation force is applied to the implantation instrument 68 in the direction of the acetabular cup 52 and generally along the central axis 70. A mallet 134 is preferably used to impart an implantation force upon the impact head 84 in a preferred embodiment, although any means for imparting an implantation force to the implantation instrument 68 may be used. Force is applied in this manner until the operating surgeon believes the acetabular cup 52 has been sufficiently inserted within the acetabular recess 51 of the pelvic bone 53. Generally, a reliable press fit is achieved whenever the outer surface of the acetabular cup 52 has "bottomed out" against the surface of the acetabular recess 51.

By the method described above, and using methods known in the art, the prosthetic orientation bar 102 and the V-shape prosthetic orientation legs 104, 106 are used to position the cup so that it is implanted in the desired orientation, including the proper angles of abduction and anteversion. As stated above, the desired angles of abduction and anteversion are achieved by orienting the implantation instrument 68 so that the prosthesis orientation bar 102 is oriented into space relative to the operating table at the desired angle of abduction, while the corresponding prosthesis orientation leg 104 is parallel to the torso of the patient. Typically, the desired angle of abduction will range between about 30°-45°, while the desired angle of anteversion will range between about 10°-20°. The exact angle for any given patient will depend on a number of factors unique to the patient, such as body type, size, and shape and the presence of complex deformities. The angles are chosen according to methods known to those skilled in the art of prosthetic hip surgery.

Figure 6:
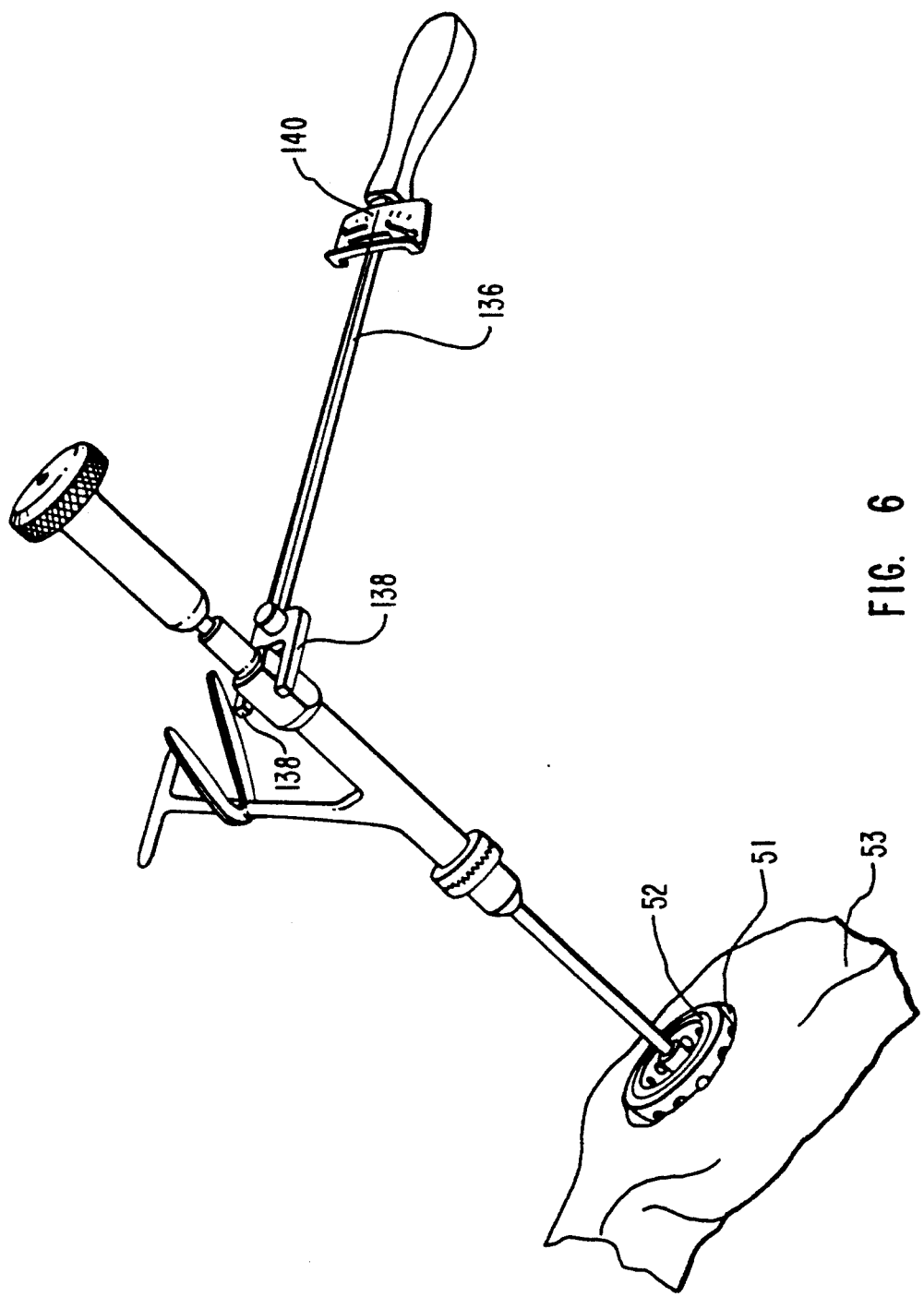
FIG. 6 shows the application of a torquing moment to the implantation device to test the stability of the acetabular cup implant.

After the acetabular cup 52 has been implanted, the operating surgeon can then test the strength or adequacy of the implant by using a torquing device, such as that shown in FIG. 6. A torque wrench 136 having parallel wrench prongs 138 engages the torquing flange 98 and is used in a preferred embodiment to impart a predetermined torquing moment to the implanted acetabular cup. The parallel wrench prongs 138 engage the flat parallel sides 100. The torque wrench is preferably equipped with a gauge 140 which measures how much torque is being applied. In this manner, the attending physician can apply a predetermined torque upon the torque wrench 136, as measured by the gauge 140, which is translated to the acetabular cup implant 52 via the implantation device 68.

If the acetabular cup implant 52 is able to resist the predetermined applied torque, the attending physician can then be more confident that the acetabular cup 52 has been successfully implanted. However, in the event that the acetabular cup 52 rotates relative to the acetabular recess 51, the physician can exert an additional implantation force by means of the mallet 134. This additional implantation force may result in the acetabular cup 52 being able to subsequently resist a predetermined torque.

However, in the event that the acetabular cup implant 52 is yet unable to resist the predetermined torque, the doctor has many options depending upon the ease with which the acetabular cup 52 is rotated. For instance, in the event that the press fit of the acetabular cup 52 within the recess 51 is so "loose" such that the implant can hardly resist any torque, it may be necessary for the physician to remove the acetabular cup 52 and reprepare the acetabular recess 51 by reboring it deeper, which often exposes softer bone tissue with better compression securement qualities. Or the surgeon may replace the first acetabular cup with a slightly larger one to create a tighter press fit between the acetabular cup 52 and recess 51. In addition, the surgeon may both reprepare the acetabular recess 51 and implant a slightly larger acetabular cup 52. These procedures are not difficult compared to replacing the cup after the patient's wounds have been closed up, and may be the preferred procedure in many cases.

However, if an acetabular cup 52 is able to resist a significant amount of applied torque, this may indicate that the fit between the acetabular cup 52 and the recess 51 is sufficiently tight such that it is unnecessary to reprepare the acetabular recess 51 or that using a larger acetabular cup 52 may result in the fracture of the pelvic bone. In this case, and in light of the fact that the press fit has a significant amount of "tightness," the doctor may only need to supplement the strength of the implant by using secondary securing means described above and known in the art. These include using a small amount of bone cement, one or more surgical screws, or surgical pegs.

It should be understood however that these secondary methods only assist in the strength of the press fit and that it is the press fit that is the primary securement means of the present invention. Although the acetabular cup implant may exhibit some degree of rotation, the fact that it is able to resist a significant amount of torque indicates that the acetabular cup has probably "bottomed out" and will likely result in a strong and durable implant once the surrounding bone is able to grow into the outer surface of the acetabular cup 52. The secondary securement means, such as the use of surgical screws or surgical pegs, merely assist in anchoring the acetabular cup until the surrounding bone is able to grow into the outer surface of the acetabular cup 52. However, in the case where bone cement is used to secure an insufficiently secure acetabular cup 52, the surrounding bone will generally be unable to grow into the outer surface of the acetabular cup 52.

In other embodiments, rather than using a torque wrench which has a gauge, it may be desirable to use a torque wrench having a mechanism for releasing after a predetermined torque has been reached. In this manner, no more torque than is desired will be applied to the acetabular cup 52. This should be contrasted with using a torque wrench that has a gauge; although the surgeon knows how much torque is being applied, the surgeon may exert more torque than is desired and thus cause unnecessary rotation of the acetabular cup implant.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. patent is:

1. A method for implanting a prosthetic acetabular cup comprising the steps of:
   providing a prosthetic acetabular cup;
   preparing a recess within the acetabular area of the pelvic bone to receive prosthetic acetabular cup;
   implanting the prosthetic acetabular cup within said recess by imparting an implantation force upon the prosthetic acetabular cup; and
   testing the stability of the implanted acetabular cup by imparting a torquing moment to said implanted acetabular cup and monitoring the relationship between the magnitude of the torquing moment and movement of the acetabular cup.

2. A method as defined in claim 1, further including the step of providing an implantation instrument comprising
   means for releasably fixing the implantation instrument to said prosthetic acetabular cup;
   means for imparting an implantation force to said prosthetic acetabular cup; and
   means for imparting a torquing moment to said prosthetic acetabular cup.

3. A method as defined in claim 2, further including the step of releasably fixing said implantation instrument to said acetabular cup, said step of imparting an implantation force to said prosthetic acetabular cup being accomplished by applying said force to said implantation instrument, and wherein said step of imparting a torquing moment to said prosthetic acetabular cup being accomplished by applying said torquing moment to said implantation instrument.

4. A method as defined in claim 3, the implantation force being applied to the implantation instrument by means of a mallet.

5. A method as defined in claim 2, said means for releasably fixing the implantation instrument to said prosthetic acetabular cup comprising a threaded hole in said cup and a threaded connector tip in an end of said instrument proximal to said cup, wherein the implantation instrument can be threadably connected to the prosthetic acetabular cup.

6. A method as defined in claim 2, said implantation instrument further including means for receiving an implantation force comprising an enlarged head attached to an end of the implantation instrument distal to the means for releasably fixing the implantation instrument to the prosthetic acetabular cup.

7. A method as defined in claim 6, said means within the implantation instrument for imparting an implantation force comprising a rigid shaft disposed between said means for receiving an implantation force and the means for releasably fixing the implantation instrument to the acetabular cup.

8. A method as defined in claim 2, said implantation instrument further including means for receiving a torquing moment.

9. A method as defined in claim 8, said means for receiving a torquing moment comprising a flange on an outer surface of the implantation instrument, said flange having a shape which conforms to the shape of a connecting end of a torquing device and wherein the torquing device can be releasably connected to said flange.

10. A method as defined in claim 8, said flange including two parallel surfaces upon which parallel forked prongs of a torquing device can fit.

11. A method as defined in claim 10, said torquing device having means to determine the amount of the torquing moment being applied.

12. A method as defined in claim 10, said torquing device having means to break an applied torquing moment once a predetermined torquing moment has been applied.

13. A method as defined in claim 8, wherein said means within the implantation instrument for imparting a torquing moment to the prosthetic acetabular cup comprise a rigid shaft disposed between the means for receiving a torquing moment and the means for releasably fixing the implantation instrument to the prosthetic acetabular cup.

14. A method as defined in claim 2, wherein the implantation instrument further includes means for receiving a stabilizing force for stabilizing the implantation instrument during the step of exerting a torquing moment.

15. A method as defined in claim 14, wherein said means for receiving a stabilizing force are rotatably connected to the implantation instrument so that the stabilizing force does not significantly oppose the totting moment.

16. A method as defined in claim 2, said implantation instrument further including orientation means for orienting the implantation instrument during the implanting step in a desired position in relation to the pelvic bone in order to implant the prosthetic acetabular cup in the desired orientation.

17. A method as defined in claim 16, the implantation instrument further including a longitudinal axis along which the implantation force is applied, wherein the orientation means comprises a prosthesis orientation bar laterally displaced from the longitudinal axis at a predetermined angle $\theta$.

18. A method as defined in claim 17, said prosthesis orientation bar being used during the implanting step to position the prosthetic acetabular cup at a predetermined angle of abduction.

19. A method as defined in claim 17, the implantation instrument further including means for selectively fixing and releasing the alignment bar to the implantation instrument, the prosthesis orientation bar being normally fixed to the implantation instrument during the step of implanting the prosthetic acetabular cup but which is selectively released to allow relative rotation between the implantinstrument and the orientation bar during a step of releasing the implantation instrument from the prosthetic acetabular cup.

20. A method as defined in claim 17, said orientation bar further including a pair of orientation legs generally disposed in a V-shaped orientation with an angle $\alpha$ therebetween.

21. A method as defined in claim 20, said orientation legs being used during the step of implantation to position the prosthetic acetabular cup at a predetermined angle of anteversion.

22. A method as defined in claim 2, the step of exerting a torquing moment also including exerting a stabilizing force to the implantation instrument, said stabilizing force maintaining said acetabular cup in substantially the same orientation as it was after the implanting step.

23. A method as defined in claim 1, the stability of the implant being determined by observing the amount of torquing moment which must be applied to cause relative movement between the prosthetic acetabular cup and a surface within the recess in the acetabular area of the pelvic bone.

24. A method as defined in claim 1, said prosthetic acetabular cup having a generally rounded outer surface proximal to the surface of said recess.

25. A method as defined in claim 24, said outer surface being generally irregular thereby allowing surrounding bone within the acetabular area of the pelvic bone to grow into and affix to said cup after it has been implanted.

26. A method as defined in claim 1, said prosthetic acetabular cup being implanted such that an outer surface of said cup has "bottomed out", thereby making substantial contact with a surface within said recess.

27. A method as defined in claim 1, further including the step of reinforcing the acetabular cup implant.

28. A method as defined in claim 1, further including the step of reinforcing the implanted acetabular cup using secondary securing means selected from the group consisting of bone cement, surgical screws, and surgical pegs.

29. A method as defined in claim 1, further including the steps of removing a first prosthetic acetabular cup inadequately implanted, implanting a second prosthetic acetabular cup according to the implanting step, and determining the stability of the implant of said second cup according to the testing step.

30. A method as defined in claim 1, further including the steps of removing an acetabular cup inadequately implanted after the step of exerting a torquing moment, repreparing the recess within the acetabular area of the pelvic bone, and reimplanting said cup.

31. A method as defined in claim 1, the diameter of said recess being slightly smaller than the diameter of said prosthetic acetabular cup.

32. A method as defined in claim 1, the prosthetic acetabular cup having a central axis, the torquing moment being substantially perpendicular to said central axis.

33. A method as defined in claim 1, the recess in the acetabular area being formed by removing bone and other surrounding tissue of the acetabular area.

34. A method as defined in claim 1, said prosthetic acetabular cup being releasably connected to an implantation instrument, said cup being designed so that it will not break or bend during the steps of imparting an implantation force and a torquing moment to said cup.

35. A method as defined in claim 1, wherein the method for implanting a prosthetic acetabular cup is successfully completed when no movement of the acetabular cup is monitored during the testing step upon imparting a predetermined torquing moment.

36. A method as defined in claim 1, wherein in the event movement of the prosthetic acetabular cup is monitored during the testing step upon imparting a predetermined torquing moment the method further including the steps of removing a first prosthetic acetabular cup and then implanting a second prosthetic acetabular cup according to the implantation step.

37. A method for implanting a prosthetic acetabular cup comprising the steps of:
providing a prosthetic acetabular cup having a threaded recess therein;
preparing a recess within the acetabular area of the pelvic bone to receive the prosthetic acetabular cup by removing bone and other surrounding tissue in the acetabular area, the diameter of said recess being slightly smaller that the diameter of said cup;
releasably fixing said acetabular cup to an implantation instrument comprising:
an end which is proximal to the prosthetic acetabular cup and another end which is distal thereto;
a threaded connector tip at the proximal end for releasably fixing said implantation instrument to said acetabular cup;
an enlarged head at the distal end for receiving an implantation force;
a rigid shaft disposed between said enlarged head and said threaded connector tip for imparting an implantation force from said enlarged head to the prosthetic acetabular cup; and
a flange disposed along said rigid rod for receiving a torquing moment, said rigid rod imparting said torquing moment from said flange to said connector tip,
said acetabular cup being threadably attached by screwing said threaded connector tip of the implantation instrument into said threaded recess of the acetabular cup;
implanting said acetabular cup in a desired orientation by exerting an implantation force upon said implantation instrument sufficient to conformingly fit the prosthetic acetabular cup within said recess within the acetabular area; and
exerting a torquing moment upon the implantation instrument whereby the stability of the implant is determined while simultaneously applying a stabilizing force to the implantation instrument, said stabilizing force maintaining said acetabular cup in substantially the same orientation as it was after the implanting step, wherein an adequate implant is determined by observing the immobility of the prosthetic acetabular cup relative to tissue in the acetabular area upon applying a predetermined torquing moment.

38. A method as defined in claim 37, said flange having a shape which conforms to the shape of a connecting end of a torquing device which is releasably connected to said flange and used to exert a torquing moment to said implantation device.

39. A method as defined in claim 38, said flange including two parallel surfaces upon which parallel forked prongs of a torquing device can fit.

40. A method as defined in claim 37, said implantation instrument further comprising a stabilizing force adapter rotatably connected to said enlarged head thereby preventing said stabilizing force from significantly opposing said torquing moment.

41. A method as defined in claim 37, wherein the implantation instrument further includes orientation means for orienting the implantation instrument during the implanting step in a desired position in relation to the pelvic bone in order to implant the prosthetic acetabular cup in the desired orientation.

42. A method as defined in claim 37, the stability of the implant being determined by observing the amount of torquing moment which must be applied to cause relative movement between the prosthetic acetabular cup and a surface of the recess within the acetabular area of the pelvic bone.

43. A method as defined in claim 37, further including the step of reinforcing the implanted acetabular cup using a secondary securement means chosen from the class consisting of bone cement, surgical screws, and surgical pegs.

44. A method as defined in claim 37, said prosthetic acetabular cup being releasably connected directly to said implantation instrument, said cup being designed so that it will not break or bend during the steps of imparting an implantation force and imparting a torquing moment to said cup.

45. An apparatus comprising an implantation instrument for implanting a prosthetic acetabular cup, the apparatus including:
- a central shaft;
- attachment means disposed at a first end of said central shaft for releasably fixing the implantation instrument to a prosthetic acetabular cup;
- means for receiving an implantation force disposed at a second end of said central shaft;
- means for imparting an implantation force disposed at a second end of said central shaft;
- means for imparting an implantation force to a prosthetic acetabular cup, said means for imparting an implantation force including said central shaft and said attachment means;
- means for receiving a torquing moment including a flange disposed on said central shaft, said flange having a surface that is complementary to the shape of a connecting end of a torquing device, said complementary surface including at least one substantially flat surface, wherein the torquing device can be releasably connected to said flange by engaging the connecting end of the torquing device and the complementary surface of the flange; and
- means for imparting a torquing moment to a prosthetic acetabular cup, said means for imparting a torquing moment including said central shaft and said attachment means.

46. An apparatus as defined in claim 45, further comprising orientation means for orienting an implanted prosthetic acetabular cup in a predetermined position in relation to the acetabular area of the pelvic bone, said orientation means being laterally disposed on said central shaft.

47. An apparatus as defined in claim 46, further including locking means for selectively releasing said orientation means whereby said central shaft of said implantation instrument can rotate relative to said orientation means.

48. An apparatus as defined in claim 47, said locking means comprising:
- a hollow actuating cuff having an interior wall, said cuff being concentric to said central shaft and disposed between the first and second ends of said shaft, said cuff having threads disposed within said interior wall, said threads conforming to threads disposed on an outer circumferential surface of said shaft wherein the rotation of said cuff relative to said shaft causes said cuff to be longitudinally displaced along said shaft;
- a hollow intermediate sleeve concentric to said shaft disposed between proximal end of said actuating cuff and a first locking clutch disposed along said shaft, said sleeve being able to slide freely along said shaft within the length defined by the proximal end of said actuating cuff and said first clutch; and
- a second locking clutch disposed on said sleeve at an end of said sleeve proximal to said first clutch, said orientation means being fixed to said intermediate sleeve.

49. An apparatus as defined in claim 48, wherein said intermediate sleeve is selectively locked to prevent rotation between said sleeve and said rod by rotating said actuating cuff until said first locking clutch is in locking engagement with said second locking clutch.

50. An apparatus as defined in claim 48, wherein said intermediate sleeve is selectively unlocked to allow free rotation between said sleeve and said rod by rotating said actuating cuff until said first locking clutch is out of locking engagement with said second locking clutch.

51. An apparatus as defined in claim 48, said first locking clutch further including a plurality of teeth disposed on a surface that is proximal to a surface of said second locking clutch, said second locking clutch further including a plurality of teeth disposed on a surface that is proximal to a surface of said first locking clutch.

52. An apparatus as defined in claim 46, wherein said orientation means comprise a prosthesis orientation bar laterally displaced from the implantation device at a predetermined angle $\theta$.

53. An apparatus as defined in claim 52, wherein said angle $\theta$ being measured by a vector defined by said orientation bar and a central longitudinal axis of the implantation instrument.

54. An apparatus as defined in claim 52, wherein said orientation bar further includes a pair of prosthesis orientation legs generally disposed in a V-shaped orientation with an angle $\alpha$ therebetween.

55. An apparatus as defined in claim 45, wherein said means for releasably fixing the implantation instrument to a prosthetic acetabular cup comprise a threaded tip disposed at the first end of said central shaft, said tip capable of being threadably connected to a threaded recess within said cup.

56. An apparatus as defined in claim 45, wherein said means for receiving an implantation force comprise an enlarged head disposed on the second end of said central shaft.

57. An apparatus as defined in claim 45, wherein said flange includes a pair of parallel surfaces upon which parallel forked prongs of a torquing device can fit.

58. An apparatus as defined in claim 45, wherein said means for imparting a torquing moment to a prosthetic acetabular cup comprise a central rod disposed between said attachment means and said means for receiving a torquing moment.

* * * * *

UNITED STATES PATENT AND TRADEMARK OFFICE
CERTIFICATE OF CORRECTION

PATENT NO. : 5,320,625
DATED : June 14, 1994
INVENTOR(S) : Kim C. Bertin, M.D.

It is certified that error appears in the above-indentified patent and that said Letters Patent is hereby corrected as shown below:

Column 6, line 29, delete "extremely" and insert therefore —difficult—

Column 15, lines 23-24, after "comprising" insert — ; —

Column 16, lines 28-29, "totting" should be —torquing—

Column 16, line 53, "implantinstrument" should be —implantation instrument—

Column 17, line 17, " ∓ " should be — " —

Column 19, lines 22-23, delete "means for imparting an implantation force disposed at a second end of said central shaft;".

Signed and Sealed this

Seventh Day of February, 1995

BRUCE LEHMAN

Attest:

Attesting Officer

Commissioner of Patents and Trademarks